(12) United States Patent
Barbarino

(10) Patent No.: US 10,058,426 B2
(45) Date of Patent: Aug. 28, 2018

(54) SYSTEM FOR TRICUSPID VALVE REPAIR

(71) Applicant: ABBOTT CARDIOVASCULAR SYSTEMS INC., Santa Clara, CA (US)

(72) Inventor: Casey M. Barbarino, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 15/215,490

(22) Filed: Jul. 20, 2016

(65) Prior Publication Data

US 2018/0021133 A1 Jan. 25, 2018

(51) Int. Cl.
*A61F 2/24* (2006.01)
*A61B 17/122* (2006.01)
*A61B 17/128* (2006.01)
*A61B 17/00* (2006.01)
*A61B 90/00* (2016.01)

(52) U.S. Cl.
CPC ........ *A61F 2/2445* (2013.01); *A61B 17/1227* (2013.01); *A61F 2/24* (2013.01); *A61B 17/1285* (2013.01); *A61B 2017/00243* (2013.01); *A61B 2017/00783* (2013.01); *A61B 2017/00867* (2013.01); *A61B 2090/037* (2016.02)

(58) Field of Classification Search
CPC ........ A61B 17/00234; A61B 17/12013; A61B 17/1227; A61B 17/1285; A61B 2017/00243; A61B 2017/00783; A61B 2017/00867; A61F 2/2463; A61F 2/2445; A61F 2/2469; A61F 2/24; A61F 2/2442; A61F 2/2448; A61F 2230/0034
See application file for complete search history.

(56) References Cited

U.S. PATENT DOCUMENTS

| 5,171,259 | A | 12/1992 | Inoue |
| 5,924,424 | A * | 7/1999 | Stevens ............ A61B 17/00234 128/898 |
| 6,129,758 | A | 10/2000 | Love |
| 7,112,207 | B2 | 9/2006 | Allen et al. |

(Continued)

FOREIGN PATENT DOCUMENTS

| WO | 9115155 A1 | 10/1991 |
| WO | 2004069055 A2 | 8/2004 |

(Continued)

OTHER PUBLICATIONS

International Search Report dated Oct. 13, 2017 from European Patent Office ISA/EP.

*Primary Examiner* — Seema Mathew
(74) *Attorney, Agent, or Firm* — David J. Pitman; Fulwider Patton LLP

(57) ABSTRACT

A system for repairing a tricuspid valve in a patient's heart; a first shaft; a first disc removably mounted on the first shaft; a second shaft coaxially aligned with, and slideable in relation to, the first shaft; a second disc removably mounted on the second shaft, wherein the second disc is positioned proximal of the first disc; and wherein the first disc includes a plurality of openings positioned on an outer perimeter of the first disc, and a first cinch wire extending through the plurality of openings and then through the catheter to the proximal end, the first cinch wire being tensionable for reducing the outer perimeter of the first disc.

8 Claims, 8 Drawing Sheets

(56) References Cited

U.S. PATENT DOCUMENTS

| | | | |
|---|---|---|---|
| 7,563,267 B2 | 7/2009 | Goldfarb et al. | |
| 8,470,028 B2 | 6/2013 | Thornton et al. | |
| 9,180,005 B1* | 11/2015 | Lashinski | A61F 2/2445 |
| 9,750,505 B2* | 9/2017 | Miles | A61B 17/1215 |
| 9,770,232 B2* | 9/2017 | Amin | A61B 17/0057 |
| 2003/0139819 A1* | 7/2003 | Beer | A61B 17/0057 |
| | | | 623/23.71 |
| 2005/0065548 A1* | 3/2005 | Marino | A61B 17/0057 |
| | | | 606/213 |
| 2006/0122646 A1* | 6/2006 | Corcoran | A61B 17/0057 |
| | | | 606/213 |
| 2007/0112380 A1* | 5/2007 | Figulla | A61B 17/0057 |
| | | | 606/213 |
| 2007/0179527 A1* | 8/2007 | Eskuri | A61B 17/0057 |
| | | | 606/213 |
| 2007/0250081 A1* | 10/2007 | Cahill | A61B 17/0057 |
| | | | 606/151 |
| 2007/0260305 A1* | 11/2007 | Drews | A61F 2/2409 |
| | | | 623/2.11 |
| 2009/0188964 A1* | 7/2009 | Orlov | A61B 17/115 |
| | | | 227/175.3 |
| 2010/0004740 A1* | 1/2010 | Seguin | A61F 2/2412 |
| | | | 623/2.18 |
| 2010/0234878 A1 | 9/2010 | Hruska et al. | |
| 2011/0060407 A1 | 3/2011 | Ketai et al. | |
| 2011/0276086 A1* | 11/2011 | Al-Qbandi | A61B 17/0057 |
| | | | 606/213 |
| 2013/0282110 A1* | 10/2013 | Schweich, Jr. | A61F 2/243 |
| | | | 623/2.11 |
| 2014/0005778 A1* | 1/2014 | Buchbinder | A61F 2/2445 |
| | | | 623/2.18 |
| 2014/0163669 A1* | 6/2014 | Ben-zvi | A61F 2/2412 |
| | | | 623/2.11 |
| 2014/0200662 A1* | 7/2014 | Eftel | A61F 2/2418 |
| | | | 623/2.38 |
| 2015/0066077 A1* | 3/2015 | Akpinar | A61B 17/0057 |
| | | | 606/213 |
| 2016/0022417 A1* | 1/2016 | Karapetian | A61F 2/2409 |
| | | | 623/2.38 |
| 2016/0030169 A1* | 2/2016 | Shahriari | A61F 2/2409 |
| | | | 623/2.18 |
| 2018/0055633 A1* | 3/2018 | Costello | A61F 2/2418 |

FOREIGN PATENT DOCUMENTS

| | | |
|---|---|---|
| WO | 2004069055 A3 | 12/2004 |
| WO | 2014018907 A1 | 1/2014 |
| WO | 2014182849 A1 | 11/2014 |

* cited by examiner

FIG. 8A
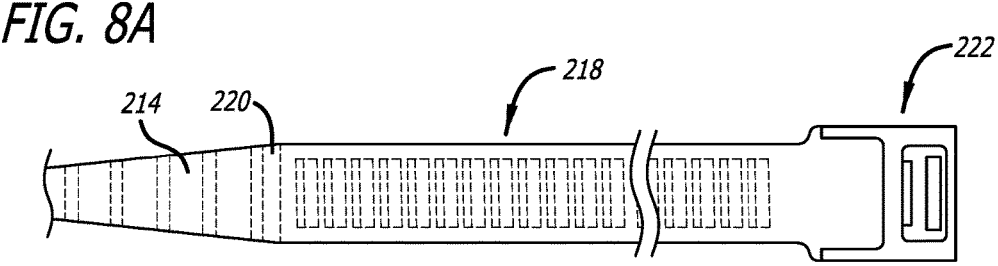
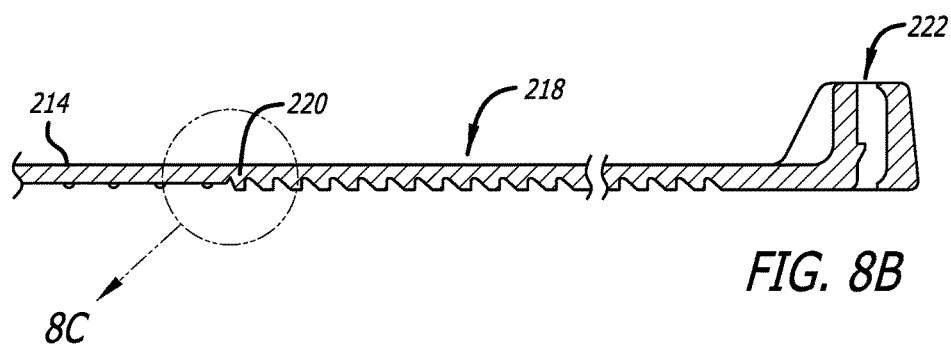
FIG. 8B
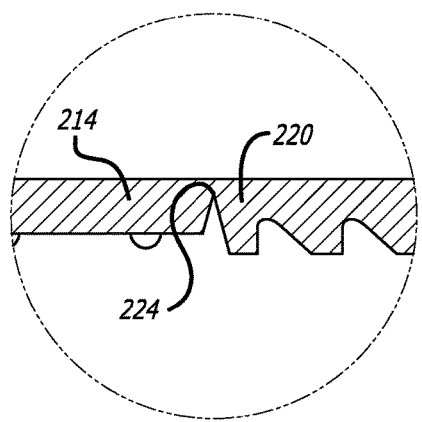
FIG. 8C

SYSTEM FOR TRICUSPID VALVE REPAIR

BACKGROUND

This invention relates to the repair of a tricuspid valve exhibiting valve regurgitation. More particularly, the invention relates to apparatus and methods suitable for a less invasive repair of a tricuspid heart valve.

FIG. 1 is a cross-sectional view of the left and right ventricles of a human heart 14 in diastole. The figure shows how the tricuspid valve 21 connects together the chambers of the right atrium and the right ventricle, and controls the flow of blood between these two chambers.

FIG. 2 is a schematic view from above of a tricuspid valve of a human heart, showing the three leaflets of the valve namely the anterior leaflet 52, posterior leaflet 54, and the septal leaflet 56, which all converge on a common point of meeting at the center of the valve.

As used herein, the term "endovascular," refers to procedure(s) of the present invention that are performed with interventional tools and supporting catheters and other equipment introduced to the heart chambers from the patient's arterial or venous vasculature remote from the heart. The interventional tools and other equipment may be introduced percutaneously. i.e., through an access sheath, or may be introduced via a surgical cut down, and then advanced from the remote access site through the vasculature until they reach heart 14. As such, the methods and apparatus described herein generally do not require penetrations made directly through an exterior heart muscle, i.e., myocardium, although there may be some instances where penetrations will be made interior to the heart, e.g., through the interatrial septum to provide for a desired access route.

The atrioventricular valves are each located at a junction of the atria and their respective ventricles. The atrioventricular valve extending between the right atrium 30 and the right ventricle 12 has three valve leaflets (cusps) and is referred to as the tricuspid or right atrioventricular valve 21. The atrioventricular valve between the left atrium 32 and the left ventricle 10 is a bicuspid valve having only two leaflets or cusps 34 and is generally referred to as the mitral valve 20.

During operation of the heart 14, the valve leaflets open during diastole when the heart atria fill with blood, allowing the blood to pass into the ventricle. During systole, however, the valve leaflets are pushed together such that the free edges of the leaflets are closed against each other along a line of coaptation to prevent the back-flow of blood into the atria. Back flow of blood or "regurgitation" through the mitral valve 20 is facilitated to be prevented when the leaflets 34 are closed, such that the mitral valve 20 functions as a "check valve" which prevents back-flow when pressure in the left ventricle 10 is higher than that in the left atrium 32.

The mitral valve leaflets 34 are attached to the surrounding heart structure along an annular region referred to as the valve annulus 40. The free edges 36 of the leaflets 34 are secured to the lower portions of the left ventricle 10 through tendon-like tissue structures, known as chordae tendineae or chordae 42. The chordae 42 are attached to the papillary muscles 44 which extend upwardly from the lower portions of the left ventricle and interventricular septum 46.

The tricuspid valve s similar to the mitral valve, but it is more three leaflets, as described above.

Tricuspid regurgitation, i.e., backward leakage of blood at the tricuspid heart valve, is typically caused by defective coaptation of the three leaflets against each other, and results in reduced pumping efficiency. Diagnosis of tricuspid regurgitation can be performed using visualization with transesophageal echocardiography or by echocardiography. In particular, defective leaflet coaptation and the site and direction of the regurgitant flow can be examined to evaluate likely modes of failure.

Tricuspid valve prolapse, i.e. degeneration of tricuspid valve leaflets, is the most common cause of tricuspid regurgitation in North America. Many cases of regurgitation can be repaired by modifications of the original valve in a procedure generally referred to as valvuloplasty. Valves that are heavily calcified or significantly compromised by disease may need to be replaced.

Successful methods have been developed for performing less invasive repairs to the mitral valve. In particular, such repairs can be performed on a beating heart such that the patient does not have to be placed on cardiopulmonary bypass.

One approach suitable for mitral valve repair is to introduce instruments via a transcatheter procedure into the heart by direct introduction through a passageway through the wall of the heart. Suitable gripping and fastening instruments have appropriate dimensions to fit through the cardiac catheter into the heart. The methods typically include gripping the edges of the two leaflets of the mitral valve, and securing them together using clasping, stitching, or suturing techniques. By connecting the leaves of the mitral valve together over a short length, the loss of tension in the leaves is reduced, and the remaining portions of the leaves have better coaptation and better perform the function of a one way valve by not permitting blood to flow in the wrong direction by regurgitation. The same approach as taken in repairing the mitral valve has been tried for repairing the tricuspid valve using clasps such as the clasp of the Mitra-Clip®.

However, methods for repairing the mitral valve do not apply conveniently to a method for repairing the tricuspid valve. One major difference is that while the mitral valve has only two leaflets extending parallel with each other and which are relatively easy to grasp simultaneously, the tricuspid valve has three leaflets 52, 54, 56 that come to a common point of meeting, as seen in FIG. 2. The mechanical problems involved in grasping all three leaflets simultaneously at a single point are far more complex than with the mitral valve, because the operator is not presented with two elongated edges to grasp, but with three triangulated points that must be grasped simultaneously. By doing this, the tension in the leaflets is increased, and coaptation is improved.

Accordingly, there is a need in the art for a novel and advantageous method to grasp and connect the three leaves of the tricuspid valve at the common point of their meeting. The present invention addresses these, and other needs.

SUMMARY OF THE INVENTION

In one embodiment, the invention is a system for repairing a tricuspid valve in a patient's heart, the system being positioned at a distal end of a catheter having a proximal end and a distal end. The system comprises a first shaft, and a first disc removably mounted on the first shaft, the first disc being in a compressed condition which has a cylindrical profile for delivery, the first disc being formed to adopt, for deployment, an expanded condition that has a concave surface facing towards the proximal end of the catheter. The system further comprises a second shaft coaxially aligned with, and slideable in relation to, the first shaft. The second shaft includes a second disc removably mounted on the second shaft, the second disc being in a compressed condition which has a cylindrical profile for delivery, the second disc being formed from shape memory metal to adopt, for deployment, an expanded condition that has a convex surface facing towards the distal end of the catheter. The second disc is positioned proximal of the first disc. Under this arrangement, the first disc includes a plurality of openings positioned on an outer perimeter of the first disc, and a first cinch wire extending through the plurality of openings and thence through the catheter to the proximal end, the first cinch wire being tensionable from the proximal end for reducing the outer perimeter of the first disc. In some embodiments, the first cinch wire includes a zip tie. The first cinch wire may include a frangible portion having a reduced dimension and configured to break when the first cinch wire is pulled from the proximal end of the catheter. In some embodiments, the system further includes a sheath which is slideably mounted to surround the second disc when in the compressed condition. In some embodiments, the first shaft includes a first rod and a first tube that slideably surrounds the first rod; and a first annulus positioned at a distal end of the first shaft to surround the first rod, and being formed of compressible material that, upon being compressed in a major direction expands in a minor direction perpendicular to the major direction. Under this arrangement, a distal end of the first tube is in operable contact with the first annulus, whereby distal movement of the first tube in relation to the first rod compresses the first annulus. In some embodiments, the second shaft includes a second rod and a second tube that slideably surrounds the second rod; and a second annulus positioned at a distal end of the second shaft to surround the second rod, and being formed of compressible material that, upon being compressed in a major direction expands in a minor direction perpendicular to the major direction. Under this arrangement, a distal end of the second tube is in operable contact with the second annulus, whereby distal movement of the second tube in relation to the second rod compresses the second annulus. In some embodiments, the second shaft defines an inner bore and the first shaft is slidingly positioned within the inner bore. In some embodiments, the first disc, when in the compressed condition, is positioned within the inner bore. In some embodiments, the second disc includes a plurality of openings positioned on an outer perimeter of the second disc, and a second cinch wire extending through the plurality of openings, the second cinch wire being tensionable from the proximal end of the catheter for reducing the outer perimeter of the second disc. In some embodiments of the system, the first disc is formed by being cut from a sheet of shape memory metal alloy, and in further embodiments, the second disc is formed by being cut from a sheet of shape memory metal alloy.

In other embodiments, the invention is a method of repairing a tricuspid valve having three leaflets in a heart of a patient. The method comprises inserting into the heart via transcatheter delivery a first disc having a concave surface with a first circumferential perimeter and a second disc having a convex surface with a second circumferential perimeter; positioning the first disc in a right atrium of the heart, with the concave surface adjacent to and facing the leaves of the valve. The second disc is positioned in a right ventricle of the heart, with the convex surface adjacent to and facing the leaflets of the valve. The first disc is moved towards the second disc, thereby trapping a portion of each of the three leaflets between the concave surface of the first disc and the convex surface of the second disc. The first circumferential perimeter of the first disc is reduced to a third circumferential perimeter that is smaller than the first circumferential perimeter. The third circumferential perimeter of the first disc is locked in in a fixed dimension. In some embodiments, reducing the first circumferential perimeter of the first disc includes applying tension to a cinching element extending along the first circumferential perimeter. In some embodiments, applying tension to a cinching element includes applying tension to a zip tie. In further embodiments, reducing the first circumferential perimeter of the first disc includes reducing the second circumferential diameter of the second disc to a fourth circumferential perimeter that is smaller than the second circumferential perimeter.

These and other advantages of the invention will become apparent when the specification is read in conjunction with the drawings and the detailed description of some embodiments.

BRIEF DESCRIPTION OF THE DRAWINGS

FIG. 8A is a component of the invention shown in plan view.

FIG. 8B is a side view of the component in FIG. 8B.

FIG. 8C is a detail of FIG. 8B identified by the circle marked "8C".

DETAILED DESCRIPTION OF THE PREFERRED EMBODIMENTS

In some embodiments, as more clearly understood with reference to the drawings, the invention is a system for repairing the tricuspid valve in the heart of a patient via a transcatheter procedure. An objective of the system is to provide a mechanism that securely grips the three common points of meeting all three of the leaflets of a tricuspid valve simultaneously, at a central point where all three leaflets meet at the center of the valve. As a consequence of this connection, the tricuspid valve is converted into a valve having three separate orifices instead of only one orifice. However after being connected, the three orifices are formed by leaflets that close more completely during the systole and therefore more effectively fulfill a function of a one way fluid valve which is to prevent regurgitation.

Figure 1:
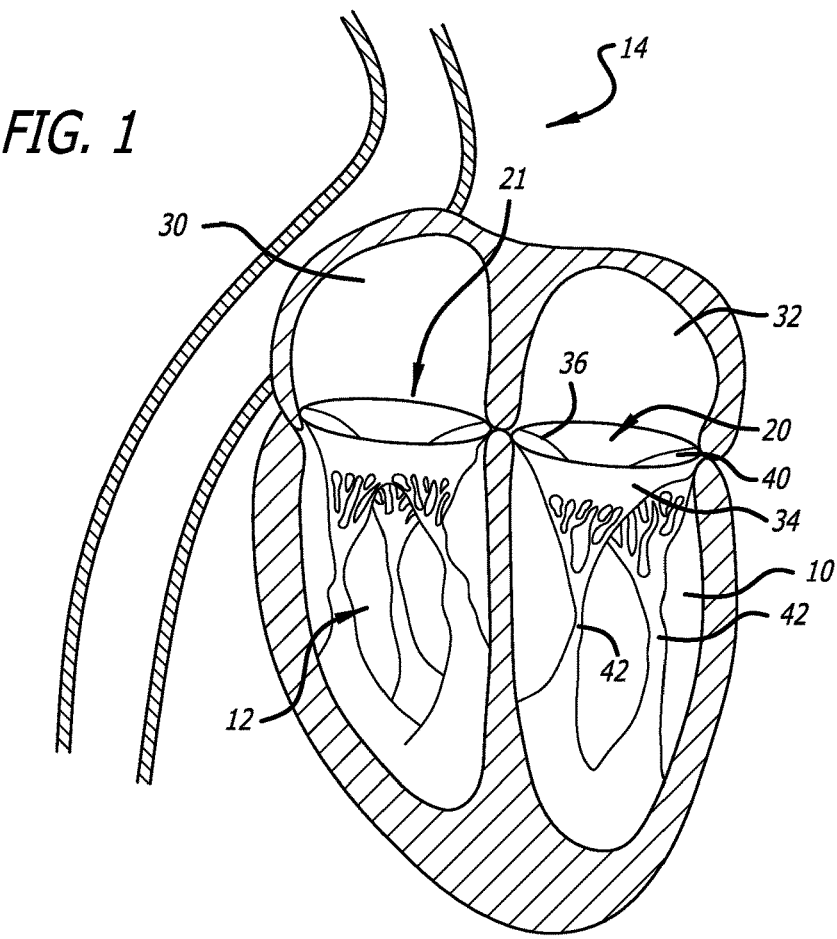
FIG. 1 is a schematic cross-sectional view of the left and right ventricles of a human heart in diastole.
Figure 2:
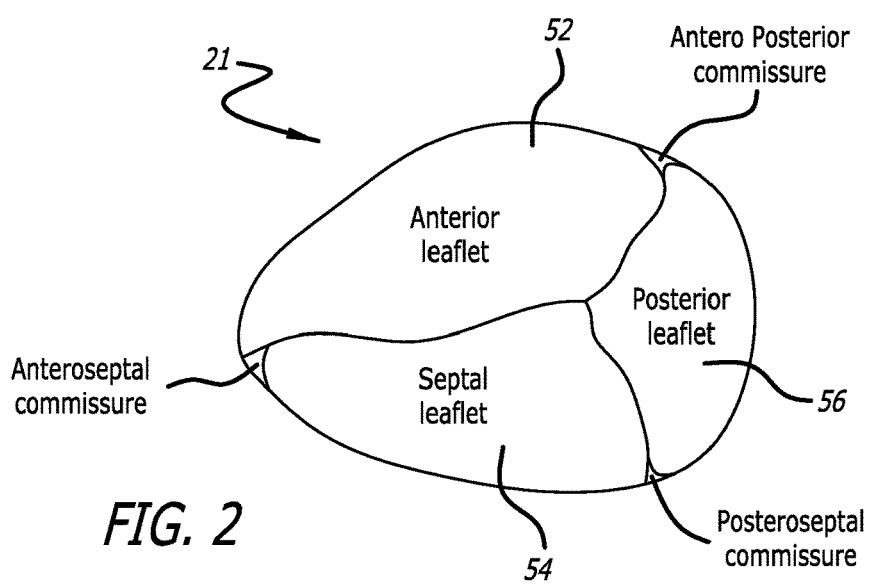
FIG. 2 is a schematic plan view of a tricuspid valve of a human heart, showing the three leaflets of the valve namely the anterior leaflet, posterior leaflet, and the septal leaflet, which all converge on a common point of meeting at the center of the valve.
Figure 3:
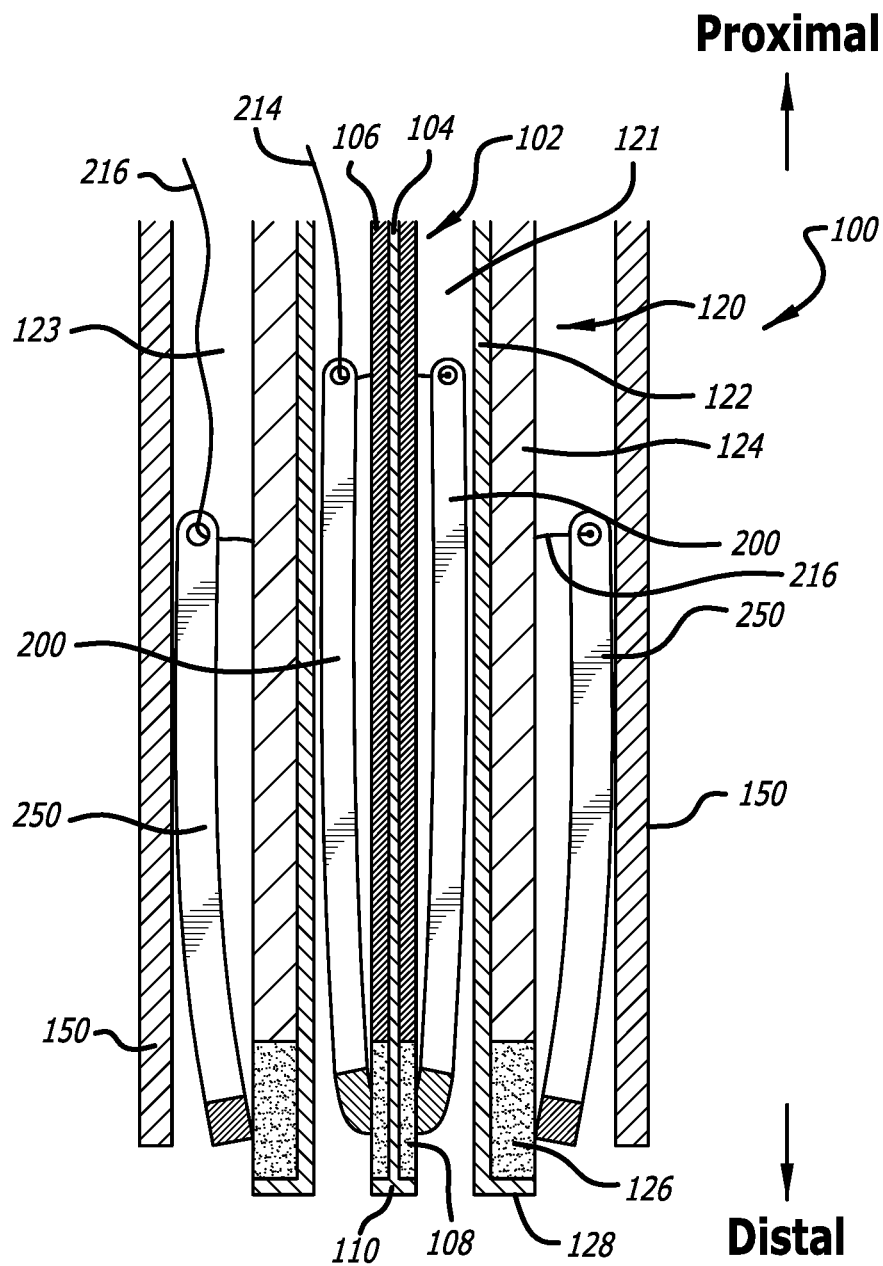
FIG. 3 is a sectional view of a system showing features of the invention, shown in a compressed condition ready for delivery to the heart of a patient.

FIG. 3 shows an exemplary sectional view of the system 100 having features of the invention in a compressed condition, positioned at the distal end of a delivery catheter—ready for delivery and then for deployment. The system includes a first disc 200 and a second disc 250. As seen in FIG. 3, the two discs are compressed to adopt cylindrical profiles suitable for insertion into tubular spaces. The first disc 200 is mounted on a first shaft 102, and the second disc 250 is mounted on a second shaft 120. The term "disc" is chosen to describe the fact that these elements are formed to have (a) an initially generally planar, circular shape and that (b) after treatment, they will have a concave/convex shape when deployed, which presents a generally circular receptacle for collecting the three leaflets of the tricuspid valve within the concavity, as will be more fully described herein; but (c) during delivery, they are compressed into a generally cylindrical shape, as more fully described.

The first shaft 102 includes three major components. A rigid first rod 104 extends along the length of the first shaft 102, and terminates at the distal end in a rigid first plate 110 extending perpendicular to the rod 104. A rigid first tube 106 surrounds the first rod, is slideable in relation to the first rod, and extends towards the distal end of the catheter. However, just at the distal end, a first collar 108 (also referred to herein as an annulus) made of flexible polymer is installed over the first rod 104 and rests on the first plate 110. This configuration provides the result that when the first tube 106 is slid distally in relation to the first rod 104, the first collar 108 is compressed in the elongate direction (i.e., in a major direction), and expands radially outwardly (i.e., in a minor direction, at right angles to the major direction). As will be further explained below, this radial expansion by the first collar facilitates the temporary mounting of the first disc 200 on the first shaft 102.

The second shaft 120 includes three major components. A rigid second rod 122 extends along the length of the second shaft 120, and terminates at the distal end in a rigid second plate 128 extending perpendicular to the rod 122. In this example, the second rod 122 has an internal bore 121 to accommodate the first shaft 102 slideably within the second rod. A rigid second tube 124 surrounds the second rod, is slideable in relation to the second rod, and extends towards the distal end of the catheter. However, just at the distal end, a second collar 126 made of flexible polymer is installed over the second rod 122 and rests on the second plate 128. This configuration provides the result that when the second tube 124 is slid distally in relation to the second rod 122, the second collar 128 is compressed, and expands radially outwardly. As will be further explained below, this radial expansion by the second collar facilitates the mounting of the second disc 250 on the second shaft 120.

In the case of both the first shaft 102 and the second shaft 120, a disc (200, 250 respectively) is affixed at a distal end, as seen in FIG. 3-FIG. 5C, by sliding the respective tube distally in relation to the relative rod, and then fixing the location of the tube in relation to the rod. The collar in each case expands into an opening (described below) in a disc, and holds the disc in fixed relation to the rod until such time as the tube is withdrawn to release the disc.

Finally, a sheath 150 is provided to surround and protect the system described above. The sheath is retractable proximally in relation to the system, to release the system during deployment as will be described below.

Figure 7:
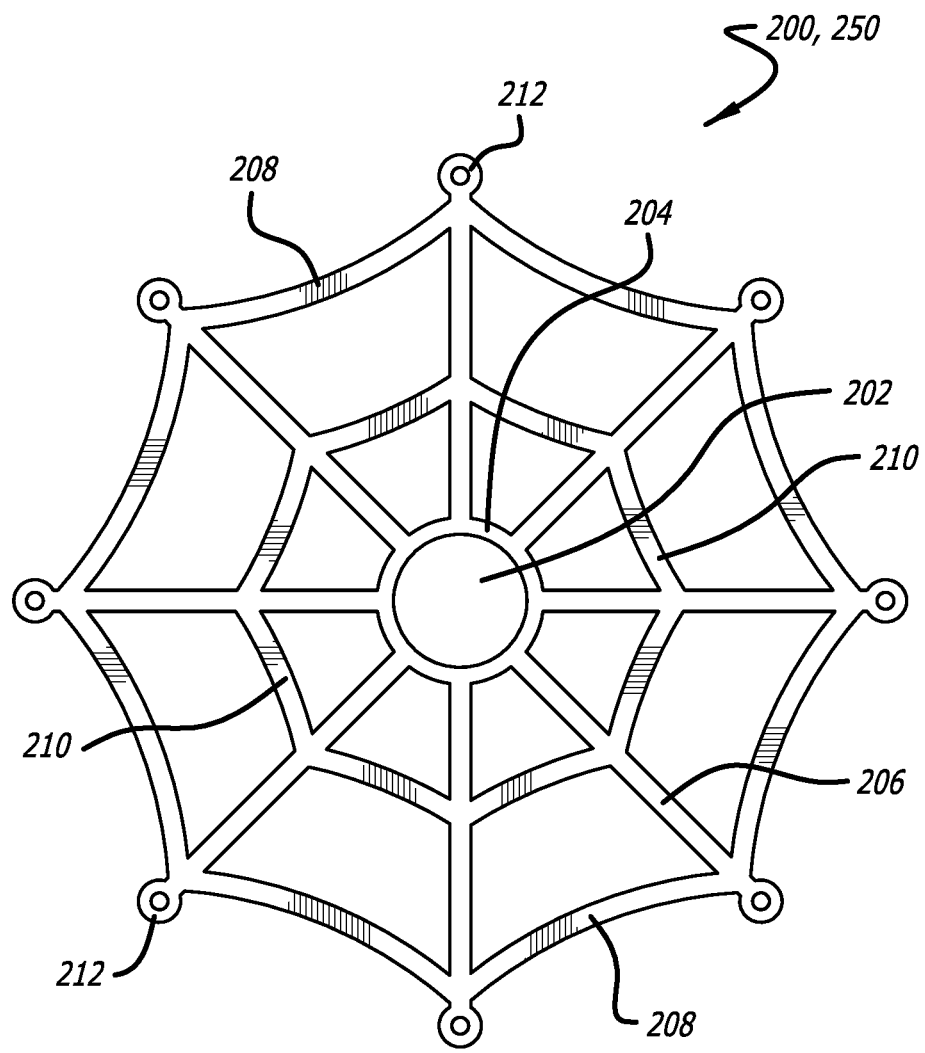
FIG. 7 is one of the components of the system of FIG. 3, a disc, shown in a plan view after being cut from a flat sheet of metal.

By way of further description of the elements comprising the system 100, the first disc 200 and the second disc 250 are described more fully with reference to FIG. 7. This figure shows a generic plan view of a disc (200, or 250) before it is folded into a cylindrical configuration for loading into the system 100. One difference between the two discs is that the first disc 200 is larger than the second disc 250. Otherwise, they possess the same general structural features. As seen in FIG. 7, the discs may be cut from a flat sheet of Nickel Titanium alloy, possessing shape memory characteristics (e.g. NiTiNol). Cutting techniques by way of laser energy are well known for this purpose. The overall shape cut out resembles that of a spider-web. (The term "web" may be used interchangeably with the term disc herein.) A central circular opening 202 is positioned at the center of the disc, surrounded by a series of struts that form a central annulus 204. Extending radially away from the annulus are a series of radially extending arms 206, each having the same length. Extending circumferentially around the outer circumference of the disc and joining the arms together are a series of first links 208. Closer to the center of the disc, a series of second links 210 extend circumferentially, also joining the arms together at a different radial position. Further links can be included as needed. As seen in FIG. 7, the links are not straight, but extend in an arc, pointing toward the center of the disc which facilitates folding of the disc between an initially flat configuration upon being cut, and a generally cylindrical, compressed configuration for delivery. The radius of the arc is chosen to permit each disc to be easily bent into a conical shape, whereby the arms may be folded parallel to a central axis extending perpendicular to the plane of the disc before it is bent, as seen in FIG. 7. At the tip of each radial arm 206, an eyelet 212 (also referred to as an opening) is cut. The eyelet is configured to allow a thread to pass through each eyelet so that the disc can be synched closed at the outer circumferential edge of the disc, as will be more fully described below. After the discs have been cut from the flat sheet of shape memory alloy, they may be given a surface texture treatment prior to permanent shape setting such as by chemical etching or by mechanically scarifying the metal. The first disc may be treated on the concave surface (proximal surface) and the second disc would be treated on the convex surface (distal surface). This surface texture treatment would allow for improved friction to hold the leaflets between the two discs.

Figure 5A:
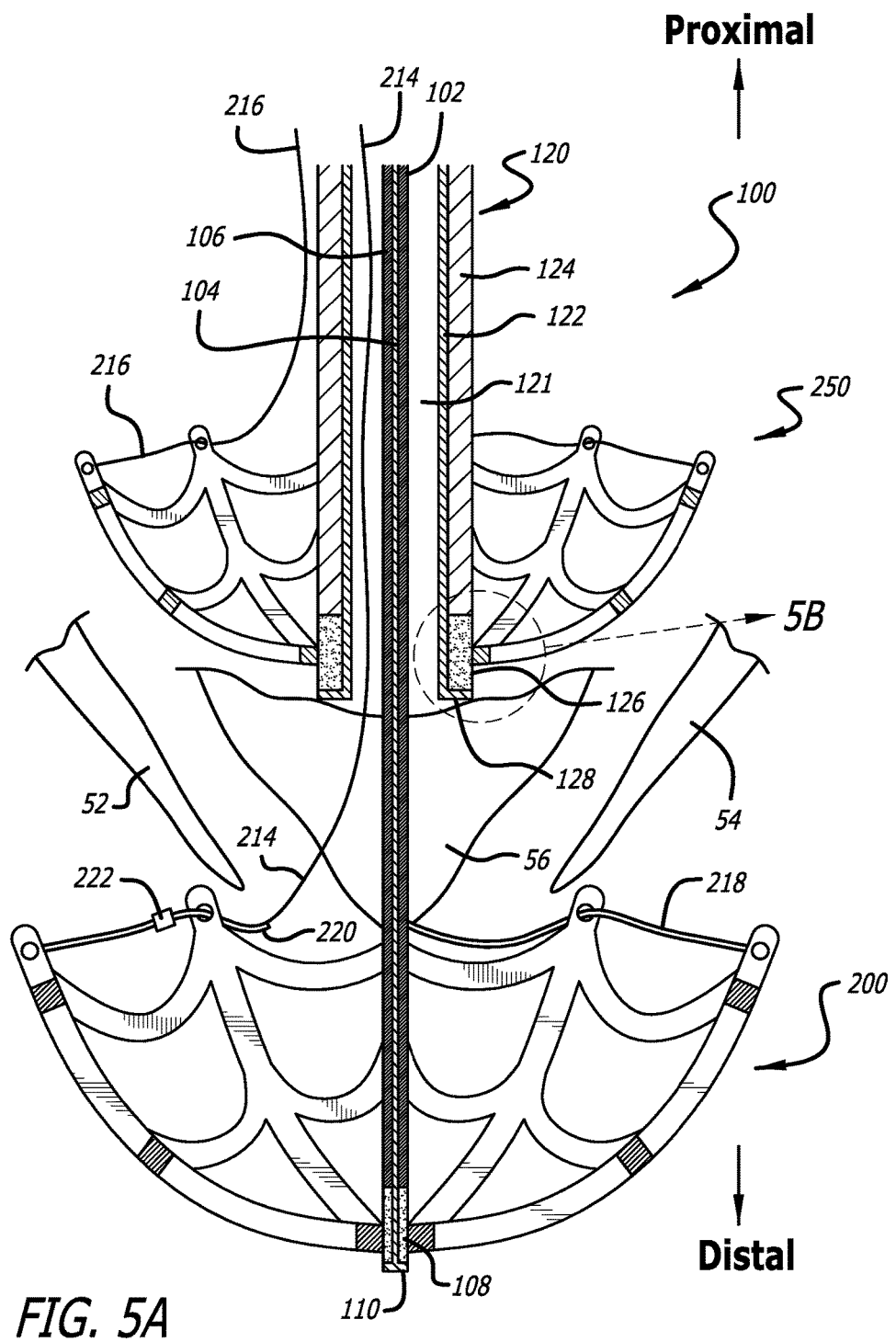
FIG. 5A is the system of FIG. 3, shown under a further partially deployed condition.
Figure 5B:
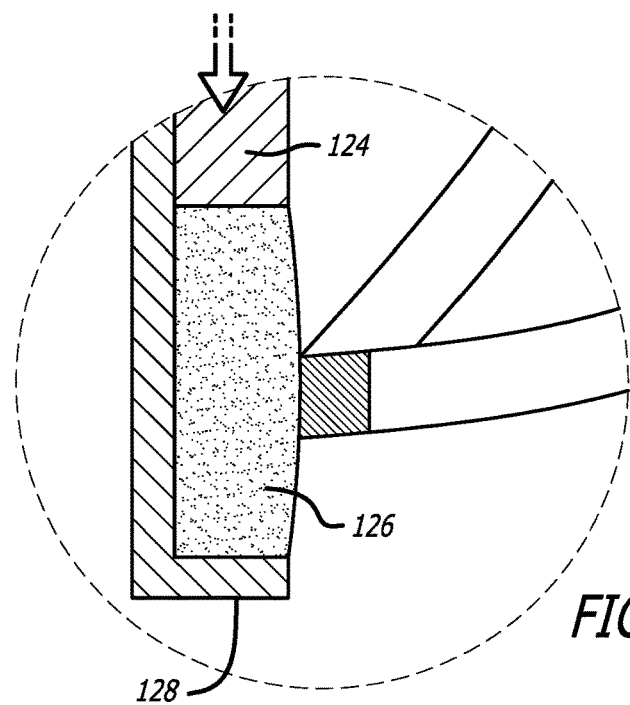
FIG. 5B is a detail view of portion of FIG. 5A circled and marked as "5B", shown in a first condition.
Figure 5C:
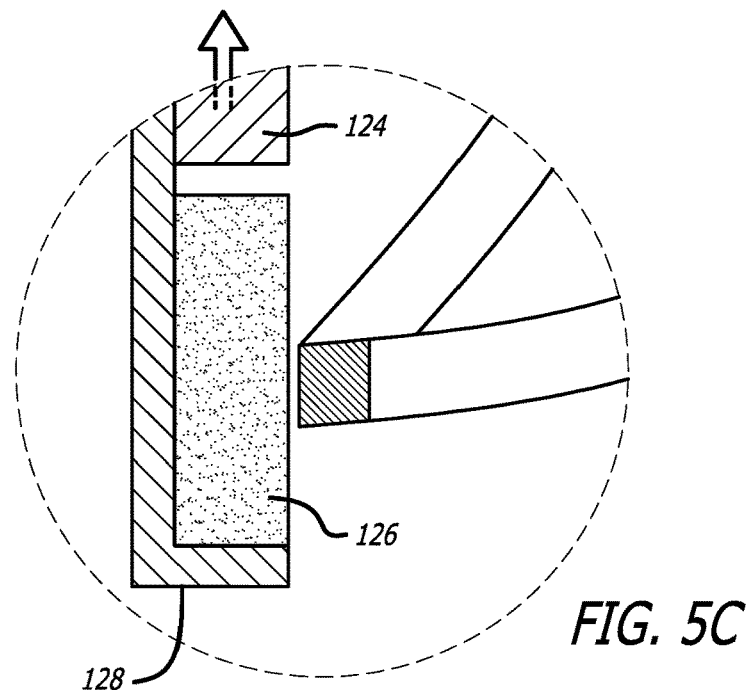
FIG. 5C is the detail in FIG. 5B, shown in a second condition.

Once the discs are cut from a flat sheet of shape memory alloy, they are given a permanent shape which is best understood with reference to FIG. 5A-FIG. 5C. The general shape given to the discs is conical, preferably with a curvature so that the disc has the general appearance of an inverted umbrella. The second disc 250 is shaped to fit within the first disc 200. The discs are then heat treated according to known methodology so that the described shape (inverted umbrella) is the default shape that the discs will assume when heated to body temperature.

Once the discs are given this default shape, they are mounted onto the first shaft 102 and second shaft 120 respectively. In order to accomplish this mounting, the second shaft is inserted into the central opening 202 of a disc, and the second tube 124 is pushed distally in relation to the second rod 122. The expanding second collar 126 locks the second disc onto the second shaft 120, whereafter the second tube is locked in relation to the second rod 122 by known technique. A second cinching wire 216 is threaded through all the openings of the second disc 250, and a free end is threaded through an internal bore 123 of the sheath 150, all the way back to the proximal end of the catheter where it may be tensioned or relaxed by the operator. The second disc 250 is folded into a cylindrical form, is cinched closed with the second cinching wire 216, and is then pushed up inside the internal bore 123 of the sheath 150. The system now has the general appearance of the system seen in FIG. 4.

Then, the distal end of the first shaft 102 is inserted into the central opening 206 of the first disc 200. The first tube 106 is pushed distally in relation to the first rod 104, thereby expanding the first collar 108. This expansion locks the first disc 200 onto the first shaft 102. The first tube 106 is then mounted onto position in relation to the first rod 104 and held there in locked condition, using known technique. A first cinching wire 214 is threaded through all the openings of the second disc, and a free end is threaded through the internal bore of the second shaft 120, all the way back to the proximal end of the catheter where it may be tensioned or relaxed by the operator. Thereafter, the first disc is closed into a cylindrical shape, and is then pushed up inside the bore 121 of the second shaft 120. The system now has the general appearance of the system seen in FIG. 3. It is ready for deployment.

The same locking action as described above may be achieved by providing an inflatable balloon mechanism for securing the mounting of each of the first disc and the second disc onto their respective shafts. For example, a balloon (not shown) may replace the first collar and the second collar respectively, each balloon having a dedicated lumen extending back to the proximal end of the catheter. Inflation of the balloon with a fluid via such lumen may cause the respective balloon to expand and thereby to trap the discs in a similar fashion to that achieved by expanding the respective collar.

A system for cinching and locking the cinch in a closed condition is now described with reference to FIG. 8A-FIG. 8C. The second cinching wire 216 need only run freely through the openings of the second disc 216 in order to permit the operator to close the second disc in the event that a problem arises and the procedure must be aborted. The first disc 200, on the other hand, must be capable of being closed permanently after the three leaflets are successfully captured between the first and the second discs. To this end, the cinching system for the first disc is fitted with a very thin zip tie 218 formed from an insoluble polymer, and this zip tie is threaded through the openings in the first disc as seen in FIG. 5A. As in the case of a typical zip tie that is known in the art, the tie 218 has a free end 220 at a first end, and a lock 222 at the opposite second end. Zip ties (also known as Cable Ties) are well known in the art, as exemplified by U.S. Pat. No. 5,956,813 and the art cited therein which are incorporated herein by reference. The free end 220 is threaded through the lock 222, so that when the free end is pulled in one direction through the lock, it cannot be pulled back in the other direction due to ratcheting means molded into the lock 222 and the free end 220. At the junction between the free end 220 and the cinching wire 214 that extends back through the bore 121 of the second shaft, a weakened frangible portion is provided so that a sharp tug on the cinching wire will break the junction at the frangible portion. In this regard, see, FIG. 8A-FIG. 8C, where a frangible zone 224 is exemplified. In this embodiment, the frangible zone includes a length of the tie which has reduced thickness in relation to the thickness in the vicinity of the frangible zone. This reduced thickness gives rise to the result that, should the tie be tensioned to a threshold amount of force, then the tie will break at the frangible zone, and at no other place along the length of the tie.

Thus, as will be explained below, the operator is able to pull the first disc closed until it adopts the configuration shown in FIG. 6. At this point, the operator gives the cinching wire a tug, which allows the cinching wire 214 to break away from the zip tie 218, and allows the first shaft and the second shaft to be subsequently removed freely from the two discs.

Figure 4:
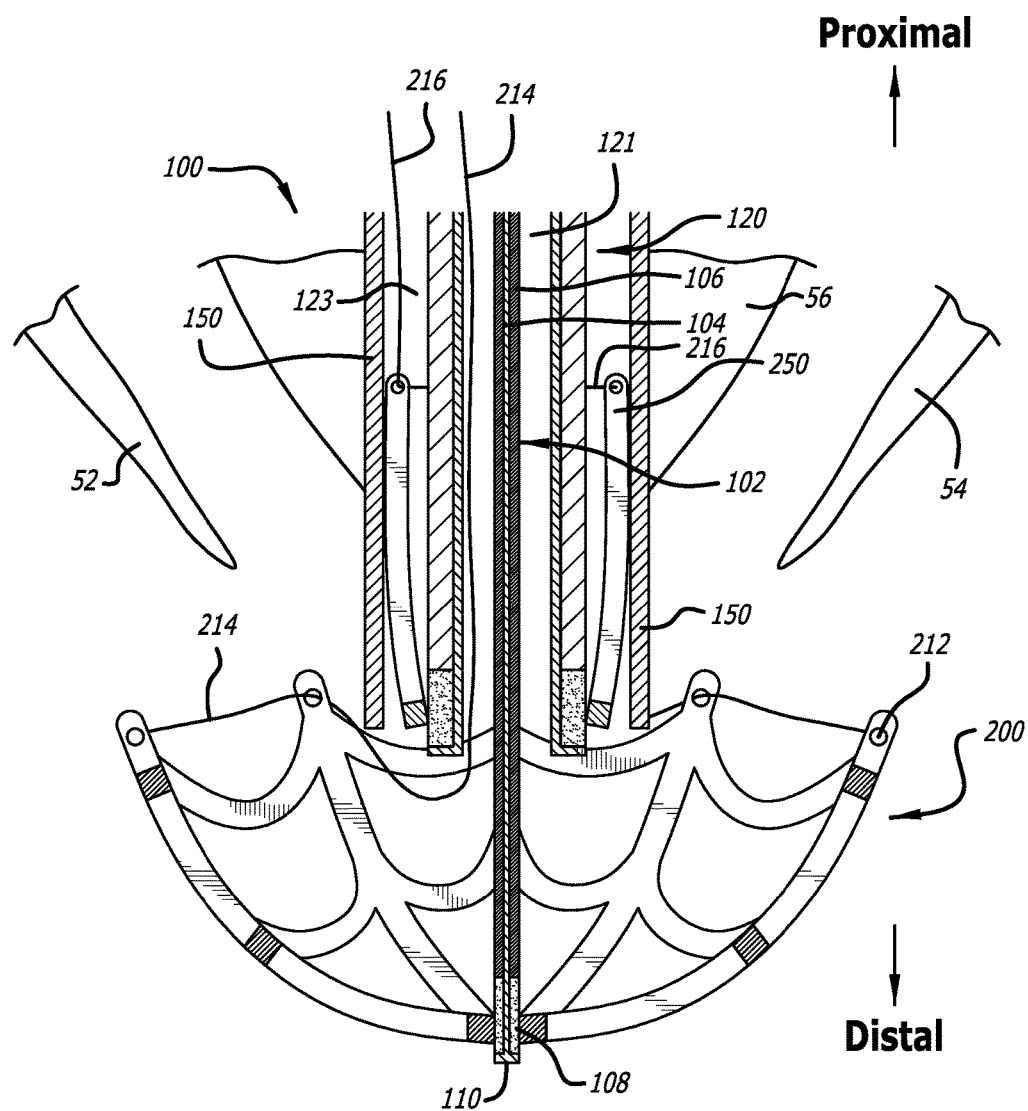
FIG. 4 is the system of FIG. 3, shown under a partially deployed condition.

Deployment of the system takes the following steps. The catheter is threaded into the right atrium of the heart of the patient according to known methodology until the system 100 contained in the distal end of the catheter is positioned directly above the tricuspid valve. The distal end is then advanced gently through the three leaflets of the tricuspid valve into the right ventricle. At this point, the first shaft 102 is advanced distally through the bore of the second shaft 120 until the first disc is completely outside the bore 121 of the second shaft and free to expand to assume its shape memory configuration, as seen in FIG. 4. It will be appreciated that the presence of the cinch wire permits the operator to abort the process at this stage if need be. The disc can be closed, and withdrawn into its initial position by pulling the cinching wire 214 and pulling the first shaft 102 back into the bore 123 of the second shaft.

When all three leaves are resting in the first disc 200, the second shaft is pulled gently upwards (proximally) and the second disc 250 is deployed by withdrawing the sheath 150 proximally to expose the second disc 250 and allow it to expand, as seen in FIG. 5A. The second disc 250 is then slowly lowered towards the first disc 200, by extending the second shaft 120 distally while holding the first shaft 102 stationary. When the three leaves are successfully trapped between the first disc 200 and the second disc 250, the operator makes a final decision whether to continue with the procedure. It will be appreciated that even at this stage the process can be aborted because the second disc can be closed by pulling on the second cinching wire 216, and withdrawing the closed second disc back into the sheath 150, followed by withdrawing the first disc as described above. However, if the operator decides to continue with the procedure, she removes the second cinching wire 216 from the system. This is possible because the second cinching wire is a continuous wire that it looped through the openings on the second disc 250. By simply pulling on one end, and releasing the other end, the second cinching wire 216 is withdrawn from the catheter.

Figure 6:
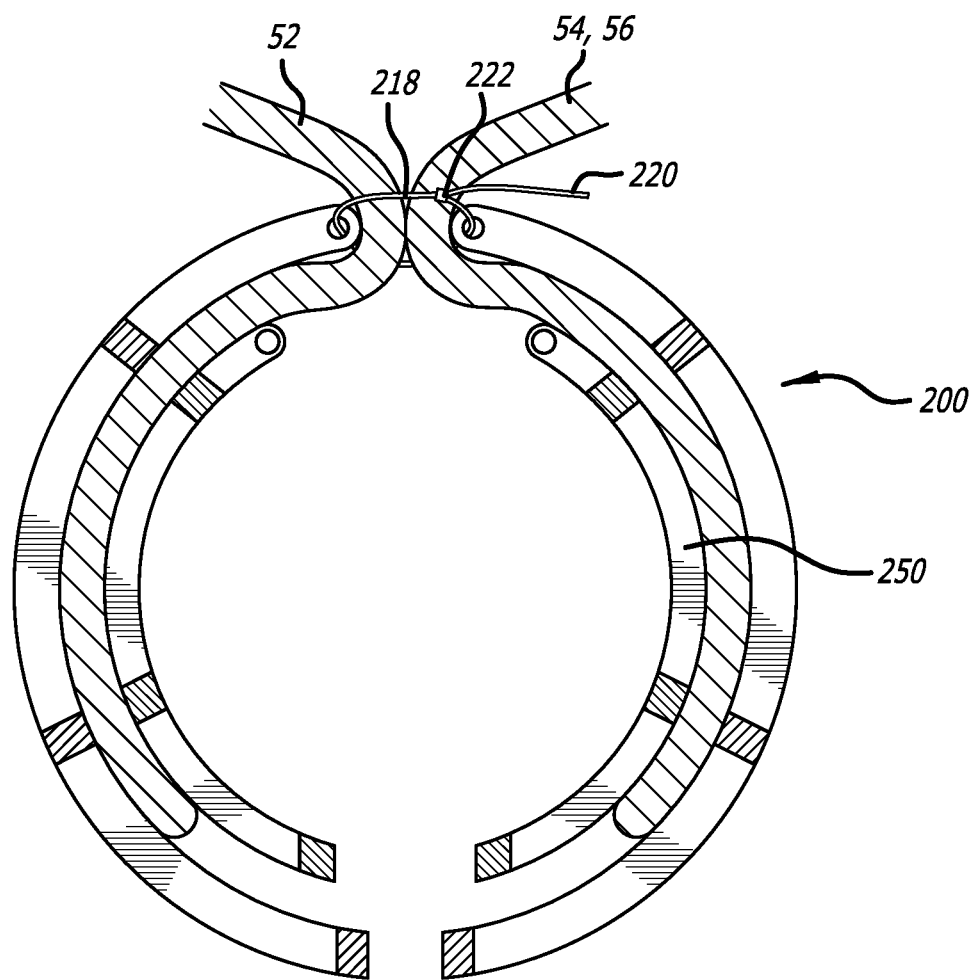
FIG. 6 is a component of the system of FIG. 3, shown having been fully deployed to grasp three leaflets of the tricuspid valve simultaneously.

Following removal of the second cinching wire 216, the first cinching wire 214 is pulled taught, thereby closing the first disc 200 into a ball shape as may be envisaged with reference to FIG. 6. A clutch mechanism of known operation (not shown) may be included on the proximal end of the catheter in order to allow the user to incrementally cinch the first disc 200. Once the first disc is closed adequately on the second disc and leaflets, the user may assess the effectiveness of the implant location in a hands free manner due to the clutch mechanism. If the user is not satisfied with the grasp or general outcome of the implant location, the clutch mechanism may be disengaged to release the cinch wire and allow for a re-grasp. Once the user is satisfied with the implant location and grasp, she may begin final movement of the clutch mechanism to pull the zip tie into its locking mechanism to fully lock the implant in its cinched position as in FIG. 6. It will be appreciated that the zip tie 218 itself must have a relatively short length in order to enable the user to abandon an attempt to grasp the leaflets and to attempt a re-grasp over a large range of movement of the first disc. Only when satisfied should the user pull the zip tie 218 itself through the lock 222, after which the process must be completed because reversal of the zip tie 218 through the lock 222 will not be possible.

The second disc 250 applies a strong force radially outwardly, and keeps the three leaves of the tricuspid valve forcibly entrapped between the two discs. The curvature of the surfaces holding the leaves provides a high degree of bollard friction, and holds the leaves securely against sliding out of the grasp of the discs.

Finally, the operator applies a tug (as distinguished from a gentle pull) on the proximal end of the first cinching wire 214, which causes the frangible portion of the wire to break at the point of connection to the zip tie 218. The operator then dismounts the first and the second discs 200, 250 from their mountings on the first shaft 102 and the second shaft 120 respectively. This dismounting is accomplished by moving the first tube 106 proximally in relation to the first rod 104, and moving the second tube 124 proximally in relation to the second rod 122, thereby decompressing the first collar 108 and the second collar 126. The decompression disengages the collars from the respective discs. The configuration of the zip tie in the closed state may leave a portion of the tie extending beyond the lock 222. However, this portion is permissible because it extends below the leaflets as seen in FIG. 6, and cannot obstruct the seal of the leaflets.

Then, the shafts are gently withdrawn proximally, leaving the three leaves connected together at a center point of the tricuspid valve, as may be envisaged by reference to FIG. 6. While it will be appreciated that a small opening may remain through the center of the disc ball, the three leaves 52, 54, 56 are tensioned to provide a functional seal along their remaining edges. This outcome will improve the overall seal between the leaf seals significantly during systole, and sufficiently to warrant the repair procedure.

Accordingly, there is described a novel system that addresses needs in the art for capturing and connecting the three contiguous points of a tricuspid heart valve. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

I claim:

1. A method of repairing a tricuspid valve having three leaflets in a heart of a patient, the method comprising:
    inserting into the heart via transcatheter delivery a first disc having a cylindrical shape in a compressed condition and a concave surface with a first circumferential perimeter in an expanded condition, and a second disc having a cylindrical shape in a compressed condition, and a convex surface with a second circumferential perimeter in an expanded condition;
    positioning the first disc in a right ventricle of the heart, passing the first disc in the compressed condition through an opening in the second disc;
    expanding the first disc from the compressed condition to the expanded condition, and locating the concave surface adjacent to and facing the three leaflets of the tricuspid valve;
    positioning the second disc in a right atrium of the heart, expanding the second disc from the compressed condition to the expanded condition, and locating the convex surface adjacent to and facing the three leaflets of the tricuspid valve;
    moving the first disc towards the second disc, thereby trapping a portion of each of the three leaflets between the concave surface of the first disc and the convex surface of the second disc;
    tensioning the three leaflets to provide a seal along opposing edges of the leaflets during systole of the heart and thereby causing the tricuspid valve to have three separate orifices for blood flow during diastole of the heart;
    reducing the first circumferential perimeter of the first disc to a third circumferential perimeter that is smaller than the first circumferential perimeter; and
    locking the third circumferential perimeter of the first disc in a fixed dimension.

2. The method of claim 1, wherein reducing the first circumferential perimeter of the first disc includes applying tension to a cinching element extending along the first circumferential perimeter.

3. The method of claim 2, wherein applying tension to a cinching element includes applying tension to a zip tie.

4. The method of claim 1, wherein reducing the first circumferential perimeter of the first disc includes reducing the second circumferential perimeter of the second disc to a fourth circumferential perimeter that is smaller than the second circumferential perimeter.

5. The method of claim 1, wherein positioning the first disc in a right ventricle includes passing the first disc, while located within a bore of a shaft in the compressed condition, through the tricuspid valve from the right atrium.

6. The method of claim 5, wherein expanding the first disc from the compressed condition to the expanded condition includes pushing the first disc from the bore of the shaft.

7. The method of claim 1, wherein moving the first disc towards the second disc includes withdrawing a shaft through the tricuspid valve, wherein the first disc is attached to the shaft.

8. The method of claim 1, wherein expanding the second disc from the compressed condition to the expanded condition includes retracting a sheath covering the second disc thereby exposing the second disc.

* * * * *